United States Patent
Steiger

(10) Patent No.: US 7,732,489 B2
(45) Date of Patent: Jun. 8, 2010

(54) TOPICAL EMULSION-GEL COMPOSITION COMPRISING DICLOFENAC SODIUM

(75) Inventor: Michel Steiger, La Tour-de-Peilz (CH)

(73) Assignee: Novartis AG (CH)

(*) Notice: Subject to any disclaimer, the term of this patent is extended or adjusted under 35 U.S.C. 154(b) by 735 days.

(21) Appl. No.: 10/524,735

(22) PCT Filed: Aug. 21, 2003

(86) PCT No.: PCT/EP03/09302

§ 371 (c)(1),
(2), (4) Date: Feb. 16, 2005

(87) PCT Pub. No.: WO2004/017998

PCT Pub. Date: Mar. 4, 2004

(65) Prior Publication Data

US 2005/0239894 A1 Oct. 27, 2005

(30) Foreign Application Priority Data

Aug. 22, 2002 (EP) .................................. 02018772

(51) Int. Cl.
*A61K 31/195* (2006.01)
*A61K 9/00* (2006.01)
(52) U.S. Cl. ........................................ 514/567; 424/400
(58) Field of Classification Search ................ 424/400, 424/401; 514/183, 567
See application file for complete search history.

(56) References Cited

U.S. PATENT DOCUMENTS

| 4,917,886 | A | | 4/1990 | Asche et al. |
| 5,350,769 | A | | 9/1994 | Kasai et al. |
| 5,374,661 | A | * | 12/1994 | Betlach, II ................ 514/772.4 |
| 5,399,342 | A | * | 3/1995 | Krzysik ....................... 424/59 |
| 6,054,484 | A | * | 4/2000 | Sekine et al. ................ 514/567 |
| 6,126,959 | A | * | 10/2000 | Levine et al. ................ 424/434 |
| 2003/0187069 | A1 | | 10/2003 | Sallin et al. |
| 2004/0101538 | A1 | | 5/2004 | Larnier et al. |

FOREIGN PATENT DOCUMENTS

| WO | WO 02/17905 | 3/2002 |
| WO | WO 02/078648 | 10/2002 |

OTHER PUBLICATIONS

Kienzler et al., "Diclofenac-Na Gel is Effective in Reducing the Pain and Inflammation Associated with Exposure to Ultraviolet Light—Results of Two Clinical Studies," Skin Parmacol. Physiol., 2005; 18: pp. 144-152.*

Magnette et al., "The Efficacy and Safety of Low-Dose Diclofenac Sodium 0.1% Gel for the Symptomatic Relief of Pain and Erythema Associated with Superficial Natural Sunburn," Eur. J. Dermatol., 2004; 14: pp. 238-246.*

* cited by examiner

*Primary Examiner*—Yong S Chong
*Assistant Examiner*—Jody L Karol
(74) *Attorney, Agent, or Firm*—Diane E. Furman

(57) ABSTRACT

The invention relates to beneficial topical pharmaceutical compositions comprising diclofenac sodium salt in unusually low amounts. The compositions represent opaque emulsion-gels, in which diclofenac is kept fully dissolved.

3 Claims, No Drawings

TOPICAL EMULSION-GEL COMPOSITION COMPRISING DICLOFENAC SODIUM

The invention concerns topical formulations comprising the well-known and widely used non-steroidal anti-inflammatory drug (NSAID) diclofenac. It is one object of the present invention to provide an advantageous emulsion-gel specifically comprising the sodium salt of diclofenac, diclofenac Na. The latter represents the most simple, cheapest, most often used (taking into account oral and other routes of administration) and best studied derivative of diclofenac.

In U.S. Pat. No. 4,917,886, a said emulsion-gel was disclosed already [see columns 2-3, composition B)]. However, the composition given there was an experimental one only and never commercialized. Its main purpose was to provide a direct comparison with the analogous crèeme composition A) comprising diclofenac Na and to demonstrate the superiority of emulsion-gels over ordinary crèmes. It had the following drawbacks: In order to obtain a sufficiently viscous emulsion-gel, especially in the presence of high amounts of lower alkanol (20% of isopropanol) and of an electrolyte (1% diclofenac Na), 1.2% of diethanolamine had to be used for neutralizing the gel-forming agent, polyacrylic acid (Carbopol 934 P).

However, nowadays the use of diethanolamine in topical formulations to be applied in humans is usually not recommended due to safety concerns about potential nitrosamine formation. It is therefore an object of the present invention to provide an emulsion-gel comprising diclofenac Na, which emulsion-gel can be obtained without neutralization with diethanolamine or other organic amines.

Moreover, a "true" emulsion-gel should be provided wherein diclofenac is fully dissolved (with no identifiable crystals of diclofenac being present in the formulation; see Test example 2 below) rather than partly suspended. This is crucial to guarantee a high, constant and reproducible permeation of diclofenac through the skin.

These aims have been achieved, surprisingly, by selecting specific components in specific amounts and so being able to neutralize the composition with ammonia, NaOH or KOH, in particular ammonia.

The invention is further characterized in that the beneficial topical formulations provided do include diclofenac, and diclofenac Na specifically, in unusually low amounts only (<0.5%, w/w). Said low dose formulations are particularly advantageous in the topical treatment of burns including sunburn. They are providing similar relief and healing as normal dose formulations (e.g. 1%) but lead to much lower exposure of the body to the active substance.

However, in order to provide a said low dose formulation, it is essential that the latter meets extraordinary standards with regard to stability, inter alia chemical stability of the active substance. Otherwise, the amount of active substance being present in the formulation over time may fall below the limits that have to be guaranteed to ensure proper pharmaceutical activity. It is therefore another object of the invention to provide a topical composition with such an extraordinary high stability profile that allows for formulating diclofenac in low doses (see Test example 1 below).

Therefore the invention relates to a pharmaceutical composition intended for topical use, which composition is in the form of an opaque emulsion-gel and which composition comprises (a) 0.02-0.4% (w/w) of diclofenac sodium salt, (b) at least 50% (w/w) of water, (c) 0-30% (w/w) of at least one C2-C4-alkanol, (d) 3-20% (w/w) of a glycol solvent selected from the group consisting of propylene glycol and polyethylene glycol (200-20000), (e) 0.2-3% (w/w) of at least one gelling agent selected from the group consisting of carbomers, (f) 2-8% (w/w) of at least one lipid forming the oily phase of the emulsion-gel, (g) 1-5% (w/w) of at least one non-ionic surfactant, and (h) a basic agent selected from the group consisting of ammonia, sodium hydroxide and potassium hydroxide to adjust the pH of the total composition to 6.5-8.

In one embodiment of the invention, said composition is devoid of any antifungal drug, e.g. devoid of terbinafine and topically acceptable salts thereof. In another embodiment of the invention, said composition is devoid of any further pharmaceutically active substance, that is to say, diclofenac sodium salt (a) is the only pharmaceutically active substance being present in that case.

All percentages given are percentages by weight (w/w), if not indicated otherwise.

Preferred are those compositions that comprise (a) 0.05-0.3% of diclofenac sodium salt, (b) 60-92% of water, (c) 0-25% of ethanol, isopropanol, or mixtures thereof, (d) 3-20% of propylene glycol, (e) 0.3-2% of at least one gelling agent selected from the group consisting of carbomers, (f) 3-7% of at least one lipid forming the fatty phase of the emulsion-gel, (g) 1-3% of at least one non-ionic surfactant, and (h) ammonia to adjust the pH of the total composition to 6.5-8.

In one embodiment of the invention, (c) is present in an amount of from 5 up to 25% and (d) is present in an amount of from 3 up to 7%, of the total composition. In another embodiment of the invention, (c) is present (or not, respectively) in an amount of from 0 up to 5%, in particular 0%, and (d) is present in an amount of from 3 up to 20% of the total composition.

In a further embodiment of the invention, (c) is present in an amount of from 0 up to 5% and (d) is present in an amount of from 3 up to 7% of the total composition. Said emulsion-gels have the additional advantage of being perceived by patients as very pleasant and non-sticky on the skin in consumer tests. Said advantage is especially pronounced, if said compositions, in addition, comprise as component (f) isopropyl myristate, and in particular a mixture of isopropyl myristate and C6-C12-alkanoic acid C12-C18-alkyl esters.

Preferably, diclofenac Na (a) is present in amount of from 0.05 up to 0.3%—especially of from 0.1 up to 0.25%—of the total composition.

Water (b) is preferably present in an amount of from 50 up to 92%, in particular of from 60 up to 90%, or of from 60 up to 80%, of the total composition.

Preferred as C2-C4-alkanols (c) are ethanol, isopropanol, or mixtures thereof; and in particular isopropanol. Preferably, (c) is present in an amount of from 0 up to 25%, in particular of from 0 up to 20%, of the total composition. In one embodiment, (c) is typically present in an amount of from 5 up to 25%, and in particular of from 10 up to 20%, of the total composition. In another embodiment of the invention, (c) is present (or not, respectively) in an amount of from 0 up to 5%—preferably of from 0 up to 4%, more preferably of from 0 up to 3%, especially of from 0 up to 2%, and more especially of from 0 up to 1%—of the total composition.

Preferably, the glycol solvent (d) is propylene glycol. Propylene glycol is 1,2-propanediol. Alternatively, polyethylene glycol (200-20000) may be used as (d), preferably polyethylene glycol (200-1000). The glycol solvent (d) is preferably present in an amount of from 3.5 up to 20%, and in particular of from 4 up to 18%, of the total composition. In one embodiment, (d) is typically present in an amount of from 3 up to 7%, and in particular of from 3.5 up to 6%, of the total composition. In another embodiment of the invention, (d) is present in an amount of from 3 up to 20%, especially of from 4 up to 18%, of the total composition.

(e) Carbomers, in the context of the present invention, are defined as homo- or copolymers of acrylic acid that are cross-linked, e.g. with an allyl ether of pentaerythritol (allyl pentaerythritol) or an allyl ether of sucrose (allyl sucrose). Copolymers are formed e.g. with minor levels of long chain alkyl acrylate co-monomers. Homopolymers are preferred. Especially preferred are carbomers 980, 940, 981, 941, 974, 934 and 910. In particular preferred are the following products provided by Noveon, Inc, Cleveland, Ohio, USA (formerly B F Goodrich): Carbopol® 980 and Carbopol® 974, and analogous carbomer products from other suppliers. Preferably, (e) is present in an amount of from 0.3 up to 2%.

(f) Lipids form the oily phase of the emulsion-gels of the invention. They can be of a vegetable or animal nature, or partly or completely synthetic. There come into consideration lipids without ester linkages, e.g. hydrocarbons, fatty alcohols or fatty acids, and lipids having ester linkages, e.g. glycerides—i.e. fatty acid esters of glycerol—, or esters of fatty acids with C1-C36-alkanols. Hydrocarbons are e.g. paraffin or petroleum jelly. Fatty alcohols are e.g. decanol, dodecanol, tetradecanol, hexadecanol or octadecanol. Fatty acids are e.g. C6-C24-, especially C10-C18-, alkanoic acids, e.g. hexanoic acid, octanoic acid, decanoic acid, dodecanoic acid, tetradecanoic acid, hexadecanoic acid or octadecanoic acid. Fatty acids further include unsaturated fatty acids, e.g. oleic acid or linoleic acid. Glycerides are e.g. olive oil, castor oil, sesame oil, it being possible for all said oils also to be hydrogenated; caprylic/capric acid triglyceride or glycerol mono-, di- and tri-esters with palmitic and/or stearic acid. Esters of fatty acids with C1-C36-alkanols are e.g. beeswax, carnauba wax, cetyl palmitate, lanolin, isopropyl myristate, isopropyl stearate, oleic acid decyl ester, ethyl oleate, or C6-C12-alkanoic acid esters—especially caprylic/capric acid esters—with saturated fatty alcohols, especially C12-C18 saturated fatty alcohols.

Preferred is a mixture of paraffin—especially liquid paraffin—and C6-C12-alkanoic acid C12-C18-alkyl esters—especially caprylic/capric acid esters with C12-C18 saturated fatty alcohols (coco-caprylate/caprate, e.g. Cetiol®LC) as well as a mixture of isopropyl myristate and C6-C12-alkanoic acid C12-C18-alkyl esters (as just characterized above). The lipid(s) (f) are preferably present in a total amount of 3-7, especially 4-6, % of the total composition. If a mixture of paraffin and coco-caprylate/caprate is used, the amount of paraffin is preferably 1.5-3%, especially 2-2.8%, and the amount of coco-caprylate/caprate is preferably 1.5-3%, especially 2-2.8%, of the total composition.

(g) A non-ionic surfactant is e.g. an ester of a fatty acid, especially a C8-C18 fatty acid, with monohydroxy or, preferably, polyhydroxy compounds, e.g. ethylene glycol, glycerol, anhydrosorbitol or pentaerythritol. Another important group of non-ionic surfactants is characterized by compounds having at least one active hydrogen, e.g. fatty alcohols—especially a C8-C18 fatty alcohol—, fatty acids—especially a C8-C18 fatty acid—, sorbitan fatty acid esters, C1-C18-alkylphenols or C8-C18-alkylamines, that all are poly(oxyethylated), preferably with from 2 up to 40 ethylene glycol or ethylene oxide units.

Examples for the above mentioned non-ionic surfactants are partial glycerin fatty acid esters, such as glycerin monostearate; partial fatty acid esters of sorbitan or polyoxyethylene sorbitan, such as sorbitan monolaurate or polyethylene glycol (5 to 20) sorbitan monostearate or monooleate; polyoxyethylene (3 to 40) fatty alcohol ethers, such as polyoxyethylene (3 to 12) lauryl ethers or polyoxyethylene (5 to 40) cetostearyl ethers; polyoxyethylene fatty acid esters, such as polyoxyethylene (8 to 100) stearate; polyoxyethylene C4-C12-alkylphenyl ethers, e.g. polyoxyethylene (nonyl or octyl)phenyl ethers; or polyoxyethylene C8-C18-alkylamines, e.g. polyoxyethylene oleylamine. Preferred are polyoxyethylene (10 to 30) fatty alcohol ethers, in particular polyoxyethylene (20) cetostearyl ether (e.g. Cetomacrogol 1000). The non-ionic surfactant (g) is preferably present in an amount of from 1.5 up to 2.5% of the total composition.

(h) Ammonia is preferably applied in the form of a concentrated aqueous solution thereof. To adjust the pH of the total composition to 6.5-8—preferably 7-8—, said concentrated aqueous solution of ammonia is e.g. present in an amount of 0.2-3% (w/w), especially 0.5-2% (w/w), of the total composition. Sodium hydroxide (NaOH) and potassium hydroxide (KOH) are e.g. applied as concentrated, e.g. 30%, aqueous solutions thereof.

The compositions of the inventions may optionally include further routine excipients known in the art, for example perfumes and antimicrobial preservatives, e.g. benzyl alcohol, benzalkonium chloride or parabens (=C1-C7-alkyl esters of 4-hydroxybenzoic acid, e.g. methyl 4-hydroxybenzoate).

In the experimental emulsion-gel "B)" disclosed in U.S. Pat. No. 4,917,886, the addition of a chemical stabilizer (sodium sulphite) was necessary to provide a chemically stable formulation. In contrast thereto, the compositions of the present invention are chemically stable without a said stabilizer. In the absence of a stabilizer, e.g. the analytical work necessary to characterize the formulations and register them at the health authorities is simplified. Therefore, a further embodiment of the invention is characterized by the compositions disclosed hereinabove and hereinbefore, which compositions are devoid of a chemical stabilizer. Chemical stabilizers are e.g. antioxidants or chelating agents, e.g. EDTA.

The topical pharmaceutical compositions according to the invention are administered in a manner known per se. For example, they are applied e.g. once, twice, or three or four times daily to the affected portions of the skin.

The invention further relates to a method of treating inflammatory diseases which comprises topically administering to a mammal in need of such treatment a therapeutically effective amount of one of the topical pharmaceutical compositions as specified herein above and below.

The manufacture of the topical pharmaceutical preparations is effected in a manner known per se, for example as described in the examples below.

The following examples are intended to illustrate the invention.

EXAMPLE 1

An emulsion gel comprising 0.1% of diclofenac Na

| Ingredients | Amount (kg/100 kg) |
|---|---|
| (a) diclofenac sodium salt | 0.10 |
| (b) purified water | 76.57 |
| (c) isopropanol | 10.0 |
| (d) propylene glycol | 5.0 |
| (e) Carbomer 980 | 0.7 |
| (f) paraffin, liquid | 2.5 |
| (f') coco-caprylate/caprate | 2.5 |
| (g) polyoxyethylene-20-cetostearyl ether | 2.0 |
| (h) ammonia, concentrated solution in water | 0.63 |
| | 100.0 |

Manufacture: (a) is dissolved in (c), (d) and (h). Said solution is added to a mixture of (b) and (e). All remaining components—(f), (f") and (g)—are heated and slowly added to the former mixture. Upon mixing a homogeneous emulsion-gel is obtained.

EXAMPLE 1a

An emulsion gel comprising 0.3% of diclofenac Na is obtained in an analogous manner to Example 1 but with using 0.30 of (a), 76.0 of (b), 0.9 of (e) and 0.8 of (h) instead.

EXAMPLE 2

An emulsion gel comprising 0.1% of diclofenac Na [without (c)]

| Ingredients | Amount (kg/100 kg) |
|---|---|
| (a) diclofenac sodium salt | 0.10 |
| (b) purified water | 74.9 |
| (c) — | — |
| (d) propylene glycol | 15.0 |
| (e) Carbomer 974P | 1.0 |
| (f) paraffin, liquid | 2.5 |
| (f') coco-caprylate/caprate | 2.5 |
| (g) polyoxyethylene-20-cetostearyl ether | 2.0 |
| (h) 30% aqueous NaOH solution | 1.5 |
| benzyl alcohol (as preservative) | 0.5 |
| | 100.0 |

EXAMPLE 3

A sprayable emulsion gel (being more fluid but still opaque and homogeneous) comprising 0.1% of diclofenac Na [without (c)]

| Ingredients | Amount (kg/100 kg) |
|---|---|
| (a) diclofenac sodium salt | 0.10 |
| (b) purified water | 86.68 |
| (c) — | — |
| (d) propylene glycol | 5.0 |
| (e) Carbomer 974P | 0.3 |
| (f) paraffin, liquid | 2.5 |
| (f') coco-caprylate/caprate | 2.5 |
| (g) polyoxyethylene-20-cetostearyl ether | 2.0 |
| (h) 30% aqueous NaOH solution | 0.42 |
| benzyl alcohol (as preservative) | 0.5 |
| | 100.0 |

The emulsion-gel is manufactured in a manner analogous to Example 1.

TEST EXAMPLE 1

The stability of the emulsion gel of Example 1 is tested via an assay of diclofenac sodium. In doing so, the formulation is stored under various conditions (temperature/relative humidity) and for various storage times, and at the end the amount of diclofenac sodium still being present is determined. The results are as follows:

| Storage time/ Condition | 25° C./60% r.h. | 30° C./60% r.h. | 40° C./75% r.h. |
|---|---|---|---|
| Start | 101% | | |
| 3 months | 101% | 101% | 100% |
| 6 months | 101% | 101% | 101% |
| 9 months | 100% | 100% | |

It is demonstrated that the active substance is completely stable even under demanding storage conditions for long periods of time.

TEST EXAMPLE 2

Microscopical Examination

The emulsion gel of Example 1 is examined under 100× magnification and scrutinized for the presence of any crystals of diclofenac sodium. Absolutely no, not even tiny, crystals of diclofenac sodium are observed. One only sees the very fine droplets of the emulsion.

The invention claimed is:

1. A pharmaceutical topical use in the form of an emulsion gel consisting of:
   (a) 0.1% (w/w) of diclofenac sodium salt,
   (b) 76.57% (w/w) of water,
   (c) 10.0% (w/w) of isopropanol,
   (d) 5.0% (w/w) of propylene glycol,
   (e) 0.7% (w/w) of Carbomer 980,
   (f) 2.5% (w/w) of liquid paraffin,
   (f") 2.5% (w/w) of coco-caprylate/caprate,
   (g) 2.0% (w/w) polyoxethylene-20-cetostearyl ether, and
   (h) 0.63% (w/w) ammonia, concentrated solution in water.

2. A pharmaceutical composition in the form of an emulsion gel for topical use consisting of:
   (a) 0.10% (w/w) of diclofenac sodium salt,
   (b) 74.9% (w/w) of water,
   (d) 15.0% (w/w) of propylene glycol,
   (e) 1.0% (w/w) of Carbomer 974P,
   (f) 2.5% (w/w) of liquid paraffin,
   (f") 2.5% (w/w) of coco-caprylate/caprate,
   (g) 2.0% (w/w) polyoxethylene-20-cetostearyl ether, (h) 1.5% (w/w) 30% aqueous NaOH solution, and
(i) 0.5% (w/w) benzyl alcohol.

3. A pharmaceutical composition in the form of a sprayable emulsion gel consisting of:
(a) 0.10% (w/w) of diclofenac sodium salt,
(b) 86.68% (w/w) of water,
(d) 5.0% (w/w) of propylene glycol,
(e) 0.3% (w/w) of Carbomer 974P,
(f) 2.5% (w/w) of liquid paraffin,
(f") 2.5% (w/w) of coco-caprylate/caprate,
(g) 2.0% (w/w) polyoxethylene-20-cetostearyl ether,
(h) 0.42% (w/w) 30% aqueous NaOH solution, and
(i) 0.5% (w/w) benzyl alcohol.

* * * * *